United States Patent [19]

Nagai et al.

[11] Patent Number: 5,650,577

[45] Date of Patent: Jul. 22, 1997

[54] LIQUID SAMPLING VALVE

[75] Inventors: Takaaki Nagai, Kobe; Teruaki Kidoh, Kakogawa, both of Japan

[73] Assignee: Toa Medical Electronics Co., Ltd., Hyogo-ken, Japan

[21] Appl. No.: 606,532

[22] Filed: Feb. 23, 1996

Related U.S. Application Data

[62] Division of Ser. No. 197,256, Feb. 16, 1994, Pat. No. 5,524,496.

[30] Foreign Application Priority Data

| Feb. 17, 1993 | [JP] | Japan | 5-10590 |
| Dec. 27, 1993 | [JP] | Japan | 5-70192 |

[51] Int. Cl.$^6$ ............................................. G01N 1/10
[52] U.S. Cl. ........................... 73/863.73; 73/864.83; 436/179
[58] Field of Search ............... 73/863.73, 864.83, 73/863.71, 863.72, 864.12, 864.82, 864.85; 422/103; 436/179

[56] References Cited

U.S. PATENT DOCUMENTS

| 1,780,828 | 11/1930 | Leach et al. . | |
| 3,885,439 | 5/1975 | Stone | 73/863.73 |
| 3,964,513 | 6/1976 | Molner | 73/863.73 |
| 3,991,055 | 11/1976 | Godin et al. . | |
| 4,702,889 | 10/1987 | Cabrera et al. | 73/863.73 |
| 4,726,932 | 2/1988 | Feier et al. | 73/863.73 |
| 4,822,569 | 4/1989 | Pellerino | 73/863.73 |
| 4,957,008 | 9/1990 | Proni et al. . | |
| 5,093,083 | 3/1992 | Preston | 73/863.73 |

FOREIGN PATENT DOCUMENTS

| 0508749 | 10/1992 | European Pat. Off. . |
| 8704370 | 7/1987 | WIPO . |
| 9007702 | 7/1990 | WIPO . |

*Primary Examiner*—Hezron E. Williams
*Assistant Examiner*—Nashmiya Ashraf

[57] ABSTRACT

A liquid sampling valve includes a fixed element having a contact surface and a movable element having a contact surface for contacting the contact surface of the fixed element; the fixed element or the movable element having measuring passageways extending to the contact surfaces, the measuring passageways having an opening for receiving and measuring a liquid sample incorporated into the opening; both the fixed element and the movable element being provided with a plurality of cleaning passageways, each having an opening at a location spaced apart from the central part of the contact surface, the location being different from the locations where the openings for the measuring passageways are provided. Movement of the movable element relative to the fixed element into a first state allows for a liquid sample to be filled into the measuring passageway, and movement into the second state allows for the liquid sample filled in the measuring passageway to be conveyed to out of the element. The plurality of cleaning passageway are arranged in such a manner that movement of the moveable element relative to the fixed element when the cleaning passageways contain cleaning liquid provides for clean areas on the contact surfaces of the elements along circumferential paths travelled by the cleaning passageways.

5 Claims, 8 Drawing Sheets

LIQUID SAMPLING VALVE

This application is a divisional of application Ser. No. 08/197,256, filed on Feb. 16, 1994 now U.S. Pat. No. 5,524,496, the entire contents of which are hereby incorporated by reference.

BACKGROUND OF THE INVENTION

1. Field of the Invention

The present invention relates to liquid sampling valves for sampling a definite quantity of liquid samples like blood, and more particularly to a liquid sampling valve provided with a cleaning function and intended for stabilizing the operation of analyzers for a long period.

2. Description of the Prior Art

Analyzers like a hemocyte counting apparatus use a liquid sampling valve for sampling liquid samples to extract a definite quantity of such liquid samples in a tubularly configured portion like a column.

Referring to FIGS. 8 and 9, a brief description is given on the construction and the operation of conventional liquid sampling valves for general use. These liquid sampling valves usually comprise two fixed elements 10, 14 and one movable element 12 sandwiched between the two fixed elements 10, 14. FIGS. 8 and 9 show two states of liquid sampling valves.

Referring to FIG. 8, liquid samples flow in the direction of an arrow A, namely through a pipette 15, an inflow passageway Q1, a measuring passageway P1, and an outflow passageway R1 to be filled in the measuring passageway P1 (referred to as a first state). The movable element 12 moves (rotates through a predetermined angle around a horizontal rotation axis) to a state shown in FIG. 9 (referred to as a second state). Samples filled in the measuring passageway P1 in the first state are conveyed in the direction of an arrow B from the passageway S12 to the passageway S11 and then to the outside of the sampling valve along with a definite quantity of diluent liquid so that liquid samples are diluted by a definite rate.

In conventional liquid sampling valves, the contact surfaces of the fixed elements and the movable element are gradually stained with samples along with an increase in the frequency of usage. When the contact surfaces are stained to a certain degree, disadvantages occur such as leakage of liquid samples from the contact surfaces, which prevents a favorable sampling operation. Conventionally, sampling valves have been regularly decomposed so that the contact surface of each element is cleaned with a cleaning liquid thereby preventing an unfavorable operation.

Liquid sampling valves intended for automation of self-cleaning are described in the following U.S. Patent Publications.

1) U.S. Pat. No. 4,702,889 (corresponding to Japanese Published Unexamined Patent Application No. SHO. 63-502454)
2) U.S. Pat. No. 4,726,932 (corresponding to Japanese Published Unexamined Patent Application No. SHO. 60-94122)
3) U.S. Pat. No. 4,957,008
4) U.S. Pat. No. 4,822,569

All the sampling valves disclosed in the above patent publications provide a passageway (passage or channel) or a groove on the surface of the element to permit a cleaning liquid to flow therethrough.

Publication 1) describes a liquid dilution and transfer valve including an outer element provided with a cleaning passageway on the periphery thereof, the cleaning passageway intercepting a leakage liquid followed by flowing a cleaning liquid therethrough to wash away the leakage liquid.

Publication 2) describes a dosing and mixing apparatus for fluid media including an internal isolating element provided with a pair of concentric channels (first and second annular channels, the second annular channel being spaced radially outward of the first annular channel) on the surface thereof as well as a radially aligned cross channels interconnecting with the first and the second annular channel thereby immediately cleaning the surface which a liquid sample contact when the liquid sample is portioned out.

Publication 3) describes a fluid sampling, metering and transfer valve assembly comprising a pair of outer stationary valve disc elements spaced apart from each other, an inner rotatable valve disc element sandwiched therebetween, and wash means comprising a pair of radially spaced circumferential concentric grooves formed along the inner and outer portions of the interior facing surfaces of at least one of outer valve disc elements, the rotatable valve disc element being rotated 360 degrees whereby to clean the facing interior surfaces of the valve assembly.

Publication 4) describes a rotary shear valve comprising two stators (front and rear stators), a first circumferentially-extending concave arced groove formed in the rear face of the front stator and a second circumferentially extending concave arced groove formed in the front face of the rear stator wherein a cleaning solution is incorporated in a third rotary position.

The sampling valve disclosed in Publication 1) cannot produce a sufficient cleaning effect because leakage material is merely intercepted in the channel and washed away.

Publications 2) and 3) describe a radially aligned concentric grooves that traverse each passageway of the sampling valve so that a cleaning liquid to be flowed in the grooves also comes into each passageway. In other words, a liquid for diluting liquid samples in the passageways and a cleaning liquid for cleaning such passageway contaminates each other (cross contamination) there. Consequently, when the cleaning liquid is different from a diluting liquid, there arises a problem that the cleaning liquid produces an unfavorable effect on liquid samples (cells such as hemocytes).

In addition, the liquid sampling valve disclosed in Publication 2) is restricted by the position of each passageway simply because radially arranged grooves are provided in such a manner that grooves traverse the passageways. In other words, the liquid sampling valve has a drawback that the position of the passageways cannot be freely set.

Furthermore, sampling valves described in Publications 3) and 4) require a special movement of elements for the cleaning operation. In Publication 3), elements are rotated once whereas in Publication 4) elements are rotated to the third rotary position.

The object of the present invention is to provide a liquid sampling valve producing a high cleaning effect free from restrictions on the arrangement of passageways and requiring no special movement for cleaning operation wherein a cleaning liquid does not produce an unfavorable effect on liquid samples owing to cross contamination of the two different kinds of liquids.

SUMMARY OF THE INVENTION

Accordingly, the present invention provides a liquid sampling valve comprising a fixed element having a contact surface and a movable element having a contact surface to be able to travel so as have surface contact with the fixed element at the contact surface thereof;

any one of the fixed element and the movable element having a measuring part on their respective contact surfaces, the measuring part having an opening and measuring a liquid sample incorporated from the opening;

both the fixed element and the movable element being provided with a plurality of cleaning passageways each having an opening at a location spaced apart from the central part of the contact surface, the location being different from the locations where the opening for the measuring part is provided;

the fixed element and the movable element assuming two states in accordance with movement of the movable element relative to the fixed element, the first state being assumed when the liquid sample is incorporated into and filled in the measuring part, the second state being assumed when the liquid sample filled in the measuring part is conveyed to the outside;

the plurality of cleaning passageways being arranged in such a manner that the openings of the cleaning passageways filled with the a cleaning liquid in any one of the fixed element and the movable element relatively travels, in accordance with the movement of itself, on the contact surface of the complementary counterpart element to clean their contact surfaces while cleaned areas are mutually joined together to make approximately one turn on the contact surfaces.

The liquid sampling valve of the present invention can be incorporated, for example, in a blood analyzing apparatus such as hemocyte counting apparatus, which is used for accurately extracting a definite quantity of blood in microliters.

The liquid sampling valve of the present invention provides a fixed element and a movable element. The fixed element is fixedly arranged and has a contact surface. The movable element provides a contact surface and is arranged in such a manner that the element can rotate or travel on a straight line in surface contact with the fixed element at the contact surface.

Both the fixed element and the movable element may be formed of ceramics such as alumina (Al2O3) into a desired configuration such as a disc-like or a square plate-like configuration. Preferably, the contact surface of each element is finished as a minutely polished planar surface to assure a close contact between the fixed and the movable element in the movement of the movable element.

Both the fixed element and the movable element are, for example, coaxially arranged. In other words, a through-hole is drilled in the central part of each element and a shaft is passed through this through-hole. The movable element is driven for the rotation and straight movement with a driving means such as an air cylinder.

In one preferable form of the liquid sampling valve of the present invention, the fixed element is constructed as one disc whereas the movable element is constructed as one disc coaxially arranged with the disc constituting the fixed element. Furthermore, in another preferable form of the liquid sampling valve of the present invention, the fixed element is constructed as coaxially arranged two discs whereas the movable element is constructed as one disc sandwiched between and coaxially arranged with the above two discs constituting the fixed element.

The fixed element is provided with a plurality of cleaning passageways penetrating the element with a plurality of openings at both surfaces of the element, the passageways serving as a path through which a cleaning liquid flows. The length and the internal diameter of these passageways may be determined so that a predetermined volume of the cleaning liquid can be contained. The movable element is provided with a plurality of cleaning passageways communicating to the cleaning passageway in the fixed element at the openings. These cleaning passageways have openings on the contact surface.

Any one of the fixed element or the movable elements has openings on the contact surface and is provided with a measuring part for measuring a liquid sample incorporated from the opening. The measuring part has an opening on the contact surface at which the measuring part is provided. The length and the internal diameter of the measuring part may be determined so that a predetermined volume of liquid samples such as blood or the like in microliters can be quantitatively taken. Such measuring part may be mounted in a predetermined number on either the fixed or movable elements. The element will be mounted at a location where it does not interfere with the openings on the cleaning passageways.

When the liquid sampling valve comprises one disc-like fixed element and one disc-like movable element, both the fixed element and the movable element have respectively one contact surface and one non-contact surface disposed back-to-back with each other. Thus, the cleaning passageways in the fixed element and the counterparts in the movable element are provided in such a manner that the contact surfaces and non-contact surfaces of the fixed and movable elements have openings. The measuring part is mounted in such a manner that the contact surface of the movable element has an opening and the non-contact surface thereof does not.

Furthermore, when the liquid sampling valve comprises coaxially arranged two disc-like fixed elements and one disc-like movable element sandwiched between and coaxially arranged with the fixed element, each of the fixed elements has one contact surface and one non-contact surface disposed back-to-back. The movable element has two contact surfaces disposed back-to-back. Here the cleaning passageways in the fixed element and the counterparts in the movable elements are provided in such a manner that the contact surface and the non-contact surface of the fixed element and the contact surfaces of the movable element have openings. The measuring part is mounted in such a manner that the two contact surfaces of the movable element have openings.

Both the fixed element and the movable element can assume at least two states in accordance with movement of the movable element. In other words, they can assume a first state in which the measuring part is filled with a liquid sample incorporated from the outside and a second state in which the liquid sample filled in the measuring part is conveyed to the outside.

The arrangement of the plurality of cleaning passageways in the fixed element and the movable element is characterized in that openings on the cleaning passageways filled with a cleaning liquid in any one of the fixed element or the movable element relatively moves on the contact surface of the complementary counterpart element in accordance with movement of the movable element, thereby cleaning the contact surface and mutually joining such cleaned areas to make approximately one turn on the contact surface.

Specifically, when the two kinds of elements have a disc-like configuration and are coaxially arranged and the movable element can be rotated through a certain angle relative to the central axis, openings for cleaning passageways in two kinds of elements are, for example, provided in the following way.

Openings on the fixed element are circumferentially provided in the number of n (n represents a natural number) around the central part of the contact surface of the fixed element so that such openings are angularly and equally spaced 360 degrees/n at an equal radial distance from the axis of the central part thereof, the distal end of the radial distance being shifted to an outer periphery of the contact surface thereof; and openings are also circumferentially provided in the number of n around the same central part so that such openings are angularly and equally spaced 360 degrees/n at an equal radial distance from the axis of the same central part, the distal end of the radial distance being shifted to the central part of the contact surface thereof so that the latter distal end of the radial distance shifted to the central part thereof is different from the former distal end of the radial distance shifted to the outer periphery thereof.

On the other hand, openings on the cleaning passageways in the movable element are circumferentially provided in the number of 2n around the central part of the contact surface of the movable element so that such openings are angularly and equally spaced 360 degrees/2n at an equal radial distance from the axis of the central part thereof, the distal end of the radial distance being shifted to the outer periphery of the contact surface thereof and being the same as the distal end of the radial distance shifted to the outer periphery of the fixed element, and openings for cleaning passageways in the movable element are also provided in the number of 2n around the same central part so that such openings are angularly and equally spaced 360 degrees/2n at an equal distance from the axis of the central part thereof, the distal end of the radial distance being shifted to the central part of the contact surface of the movable element so that the distal end of the latter radial distance shifted to the central part thereof is different from the distal end of the former radial distance shifted to the outerpheriphery thereof, the latter distal end shifted to the central part of the contact surface of the movable element being the same as the distal end shifted to the central part of the contact surface of the fixed element.

Here, 4 is selected as n in the following embodiment, but n is not always limited to 4. For example, 7 can be selected. Furthermore, the range of the natural number preferably ranges between 2 to 10.

When the two kinds of elements have a disc-like configuration, and are mutually coaxially arranged, and the movable element can be rotated through a certain angle relative to the central axis, the size of the two elements are determined in the following way.

The diameter of each of both elements is set to about 40 to 50 mm, the thickness thereof to about 5 mm, the diameter of each cleaning passageways to 2 mm, and the diameter of the measuring passageway to 0.8 to 3 mm.

When both the fixed element and the movable element each having openings of cleaning passageways thus provided assume a first state, n openings at the location shifted to the outer periphery in the fixed element are opposed to n alternate openings out of 2n openings at the location shifted to the outer periphery in the movable element while the remaining n openings at the location shifted to the central part of the fixed element are opposed to the alternate n openings out of 2n openings at the location shifted to the central part of the movable element.

Then, when the movable element is rotated from the first state through 360 degrees/2n relative to the central axis to allow the fixed and movable elements to assume the second state, the n openings at the location shifted to the outer periphery in the fixed element are opposed to different n alternate openings out of the 2n openings at the location shifted to the outer periphery in the movable element while the n openings at the location shifted to the central part in the fixed element are opposed to the remaining n alternate openings out of the 2n openings at the location shifted to the central part in the movable element.

In the liquid sampling valve in which the fixed and movable elements are provided with openings for cleaning passageways as shown in the above example, the rotation of the movable element through 360 degrees/2n with cleaning liquid filled in each cleaning passageway in two kinds of elements allows openings for cleaning passageways in one element to relatively rotate or move on the contact surface of the complementary counterpart element which surface contacts with the former element. This enables cleaning the contact surface of the latter complementary counterpart element with the cleaning liquid. Thus cleaned areas have two kinds of traces which make approximately one turn on the contact surface by the formation of two kinds of arc-like portions small and large respectively having a central angle of 360 degrees/2n at 360 degrees/2n locations followed by the joining of the respective kind of arc-like portion. Therefore, the liquid sampling valve of the present invention with the above construction can provide the following effect.

(1) The liquid sampling valve of the present invention does not require a complicated processing, and cleaning passageways can be made with a simple processing unlike the conventional counterpart of the liquid sampling valve because the valve is so constructed that the plurality of cleaning passageways are provided on the fixed element and the movable element and the movement of the movable element after a cleaning liquid is filled in the passageways allows cleaning by small areas in a ring-like configuration the contact surfaces at which the fixed element and the movable element contact with each other.

(2) In addition, stains adhering on the surface of the elements can be wiped off with the edge portion of the openings of the cleaning passageways, which extremely enhances the cleaning effect.

(3) Since the cleaning passageways and other passageways such as the passageway for measuring liquid samples do not interfere with each other, diluent liquid for diluting samples in the passageway and cleaning liquid do not contaminate each other.

BRIEF DESCRIPTION OF THE DRAWINGS

To make the present invention clear and by way of example, reference is made to the drawings in which.

DETAILED DESCRIPTION OF PREFERRED EMBODIMENTS

In a liquid sampling valve of the present invention, a fixed element and a movable element are preferably so constructed that the movable element can be rotated through a certain angle and each of cleaning passageways are concentrically provided on each element at an equal angle to each other.

Furthermore, in the liquid sampling valve of the present invention, preferably the configuration of the opening in the cleaning passageways is either approximately circular or approximately elliptical.

Still furthermore, preferably the plurality of cleaning passageways in the plurality of elements mutually communicate with each other so that a plurality of fluid paths can be formed, and communicating passageways connecting the plurality of fluid paths are provided. These communicating passageways either take the form of a loop-like passageway, for example, projecting out of the element, or a groove-like passageway provided on the surface of the element.

When a cleaning liquid fills the cleaning passageways to move the movable element, the cleaning passageway filled with the cleaning liquid relatively travels on the contact surface of the complementary counterpart element facing to itself. The cleaning passageways remove stains by traveling in such a manner that they wipe off stains on the surface of the element at the edge of the opening of the passageway.
Embodiment The present invention will be detailed in conjunction with the accompanying drawings. However, the shape of the constituent apparatus described in embodiments and the relative positions thereof are not intended to restrict the scope of the present invention unless otherwise stated. They should be regarded as an illustrative example.
Embodiment 1

Figure 1:
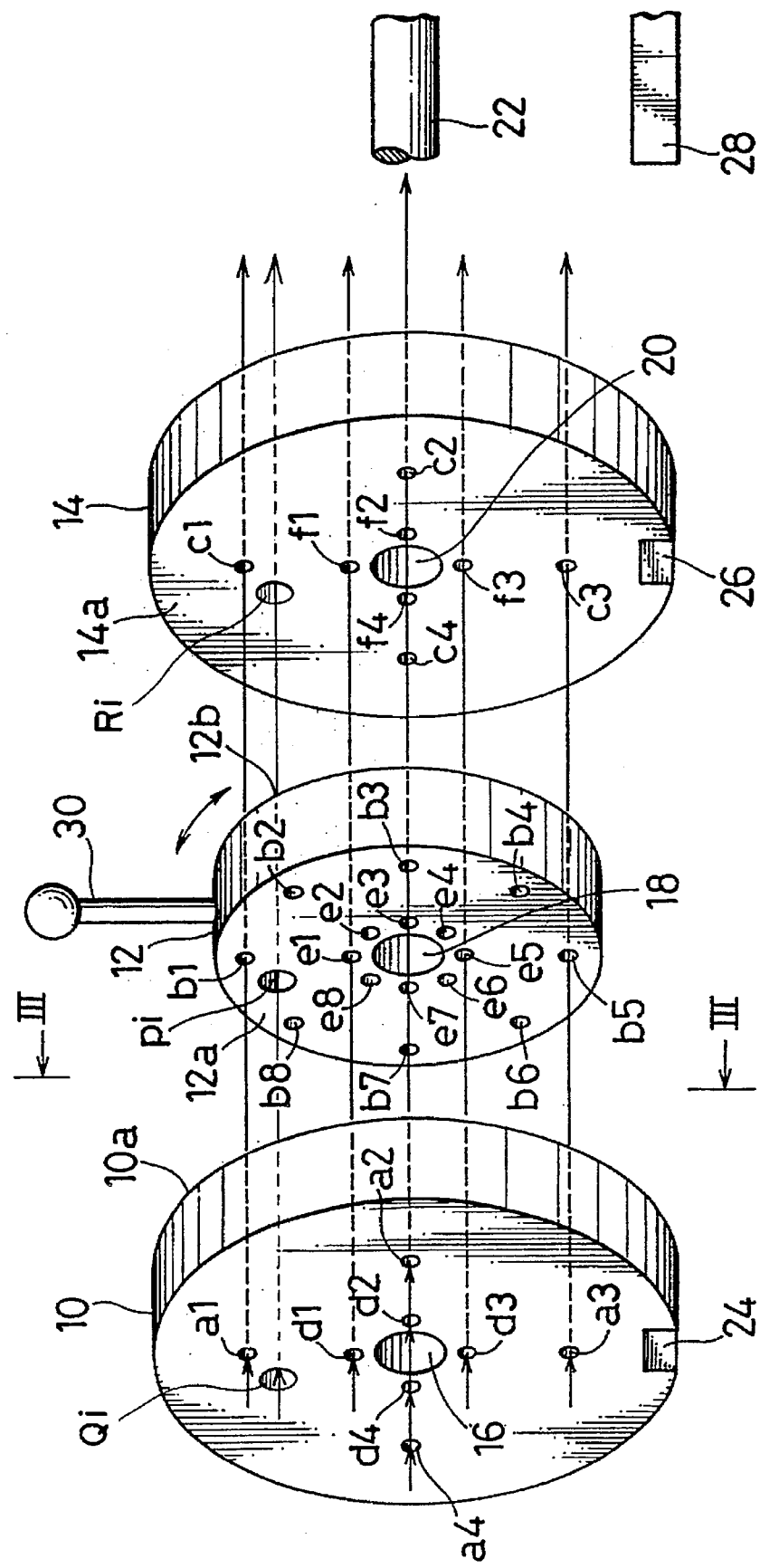
FIG. 1 is a view showing Embodiment 1 of a liquid sampling valve of the present invention, the view being a perspective decomposition view showing a first state (state in which liquid samples are absorbed in the measuring passageway) in which a measuring passageway in a movable element is filled with a blood sample.
Figure 2:
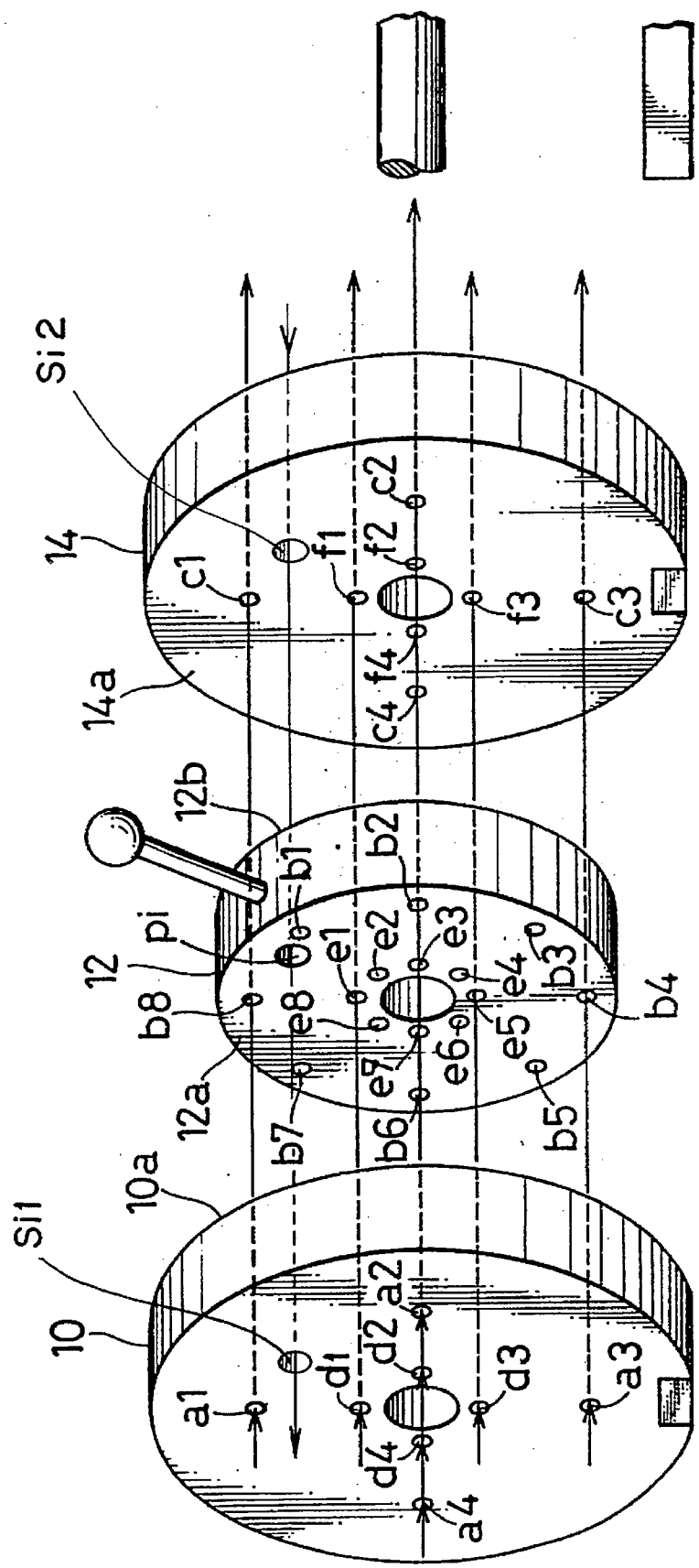
FIG. 2 is a perspective decomposition view showing a second state (state in which liquid samples are conveyed out of the measuring passageway) in which the movable element is rotated through a certain degree of angle from the first state shown in FIG. 1.

FIGS. 1 and 2 are perspective decomposition views showing one embodiment of a sampling valve of the present invention. The sampling valve comprises two disc-like fixed elements 10, 14 and one disc-like movable element 12 sandwiched between two fixed elements 10, 14.

FIG. 1 shows a first state (sample filled state) in which a blood sample is filled in a measuring passageway Pi of the movable element 12 in the movement similar to the conventional general sampling valve. FIG. 2 shows a second state in which the movable element 12 rotates from the first state through a definite angle 8 (45 degrees in this embodiment) relative to the fixed elements 10, 14. Each element 10, 12 and 14 provides a hole 16, 18 and 20 at the center thereof. The shaft 22 penetrates through these holes 16, 18 and 20. Then these elements 10, 12 and 14 mutually comes into close contact to each other. Reference Numeral 24 and 26 designate key grooves, 28 a key, and 30 a arm-shaped operation member, which is rotated by a drive source (not shown in the drawings).

On the outer periphery of the movable element 12, eight cleaning passageways bi: (b1, - - - -, b8) are concentrically provided at an angle equal to the above angle 8 through which the movable element is rotated. The cleaning passageway bi is concentrically provided by penetrating the movable element 12. On the internal periphery of the movable element 12 is provided still other eight cleaning passageways ei: (e1, - - -, e8) at an angle equal to the angle 8 on concentric circles having different radii. These passageways ei are also provided by penetrating through the movable element 12. On one fixed elements 10 are provided two kinds of cleaning passageways aj and dj respectively communicating to the cleaning passageways bi and ei in the movable element 12. On the other fixed element 14 are provided cleaning passageways bi and ei respectively communicating to cleaning passageways cj and fj in the movable element 12.

Each of the passageways aj and cj are provided in fours. In other words, passageways a1, c1 communicate to the passageway b1 (located adjacent to the passageway b8 described later) in the first state while communicating to the passageway b8 in the second state (located adjacent to passageway b7 described later).

Passageways a2 and c2 communicate to passageway b3 (located adjacent to passageway b2) in the first state while communicating to passageway b2 (located adjacent to passageway b1) in the second state.

Passageways a3 and c3 communicate to passageway b5 (located adjacent to passageway b4) in the first state while communicating to passageway b4 (located adjacent to passageway b3) in the second state.

Passageways a4 and c4 communicate to passageway b7 (located adjacent to passageway b6) in the first state while communicating to passageway b6 (located adjacent to passageway b5) in the second state.

Passageways dj and fj are provided, respectively, in fours. In other words, passageways d1 and f1 communicate to passageway e1 (located adjacent to passageway e8 described later) in the first state while communicating to passageway e8 (located adjacent to passageway e7 described later) in the second state.

Passageways d2 and f2 communicate to passageway e3 (located adjacent to passageway e2) in the first state while communicating to passageway e2 (located adjacent to passageway e1) in the second state.

Passageways d3 and f3 communicate to passageway e5 (located adjacent to passageway e4) in the first state while communicating to passageway e4 (located adjacent to e3) in the second state.

Passageways d4 and f4 communicate to passageway e7 (located adjacent to passageway e6) in the first state while communicating to passageway e6 (located adjacent to passageway e5) in the second state.

Each of the cleaning passageways aj, bi, cj, dj, ei and fj in three elements 10, 12 and 14 are provided with a different length in the direction of the radii thereof so that they do not interfere with other passageways such as the measuring passageway Pi.

The supply of a cleaning liquid respectively from passageway aj (a1, a2, a3 and a4) (or from passageway cj: (c1, c2, c3 and c4)) in the first state shown in FIG. 1 will result in the discharge of the cleaning liquid from passageways cj: (c1, c2, c3 and c4) via a first group of passageway bh comprising cleaning passageways b1, b3, b5 and b7 included in passageway bi provided on the movable element 12. This causes each passageway aj, bh and cj to be replete with the cleaning liquid.

Then the supply of the cleaning liquid from passageway aj: (a1, a2, a3 and a4) (or from passageway cj: (c1, c2, c3 and c4) in the second state shown in FIG. 2 will result in the discharge of the cleaning liquid respectively from passageway cj: (c1, c2, c3 and c4) via a second group of passageway bk comprising b2, b4, b6 and b8 included in passageway bi of the movable element 12. This causes each passageway aj, bk and cj to be replete with the cleaning liquid.

The same thing holds true of a case in which the cleaning liquid is filled in passageways dj, ei, and fj.

When the movable element 12 rotates with each passageway aj, bi, cj, dj, ei, and fj filled with the cleaning liquid, the cleaning liquid held in the cleaning passageway of a certain element cleans the contact surface of other elements by relatively moving on it.

Figure 3:
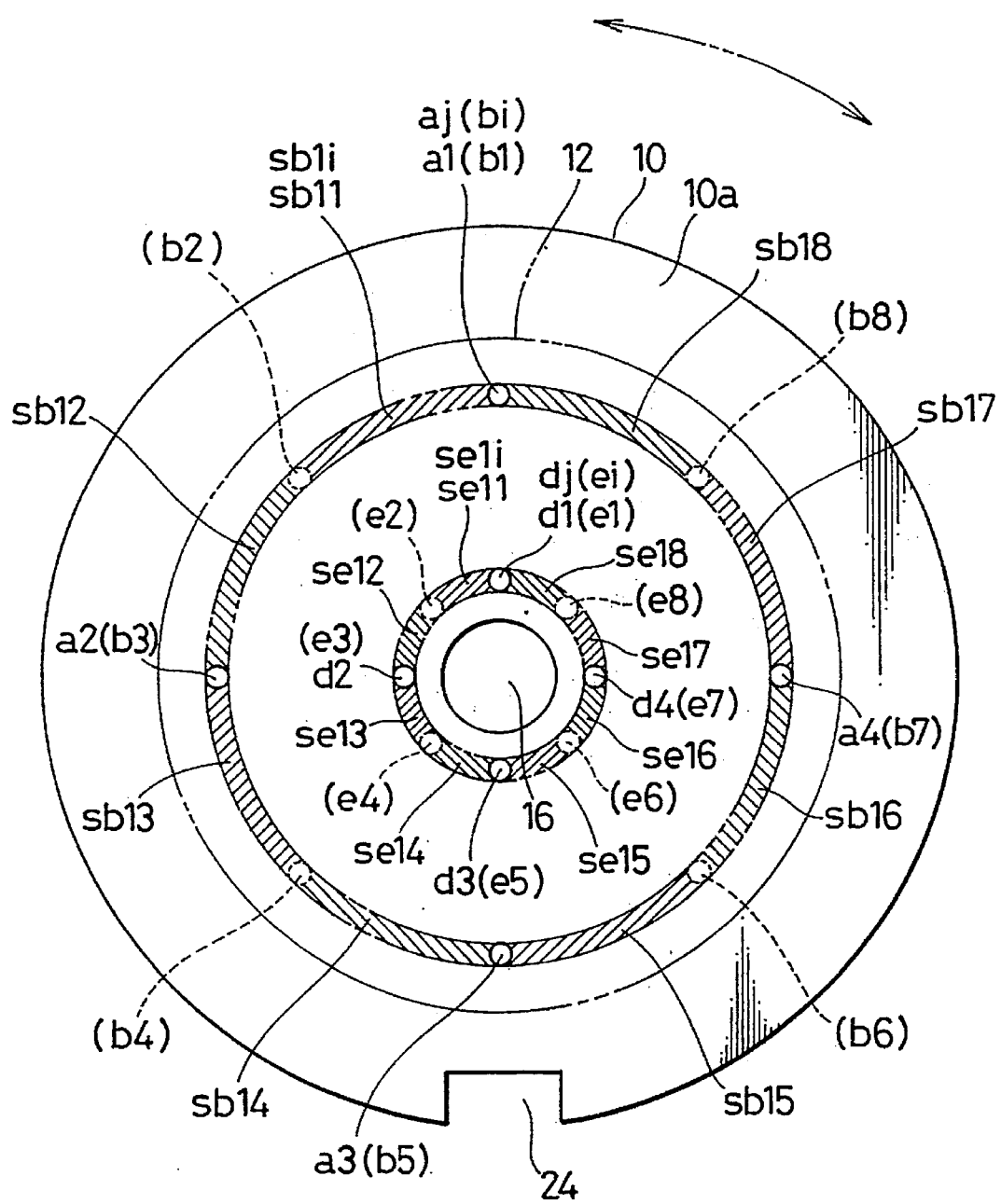
FIG. 3 is a right side view for illustrating the right side of one of the fixed elements as seen from the direction of an arrow A shown in FIG. 1.

FIG. 3 is a view for illustrating areas which have been already cleaned as seen from the direction of an arrow A shown in FIG. 1. In other words, FIG. 3 is a right side view of one of the fixed elements 10 shown in FIG. 1. Reference Numerals Sb1i: Sb11 through Sb18, Se1i: Se11 through Se18 designate areas on the contact surface 10a of the fixed element 10 which have been cleaned with passageways bi: b1 through b8, ei: e1 through e8 of the movable element 12. Cleaned areas Sb1i: Sb11 through Sb18 and Se1i: Se11 through Se18 are mutually communicated to each other so as to form a ring-like loop. Surfaces 12a, 12b and 14a of other elements 12 and 14 are also cleaned in the same manner with other cleaning passageways filled with cleaning liquid. Cleaning passageways may not be necessarily equally spaced.

As described above, the sampling valve of the present invention does not require a complicated processing. Cleaning passageways can be made with a simple processing.

In addition, the contact surface of elements can be favorably cleaned with openings of such passageways. In other words, the liquid sampling valve does not clean the surfaces of the elements thereof by letting a cleaning liquid to flow through grooves. The liquid sampling valve provides instead a plurality of cleaning passageways to clean polished surfaces of mutually facing elements little by little by transferring the movable element 12 after filling a cleaning liquid in the cleaning passageways. Consequently the elements are cleaned in a ring-like configuration. In the process, the liquid sampling valve can remove stains by allowing the cleaning liquid to contact the surface of the elements as well as removing the stains on the surface at the edge of opening of the passageway by wiping them off. This produces a very high cleaning effect.

In addition, cleaning passageways do not interfere with other passageways such as the measuring passageway, and therefore liquids do not contaminate each other.

By the way, in Embodiment 1, cleaning passageways in the elements 10, 12 and 14 are provided both on the outer circumferential portion and the inner circumferential portion of the contact surface. However, the cleaning effect is favorable when cleaning passageways are provided only on the outer circumferential portion (only passageways aj, bi, and cj).

Figure 4:
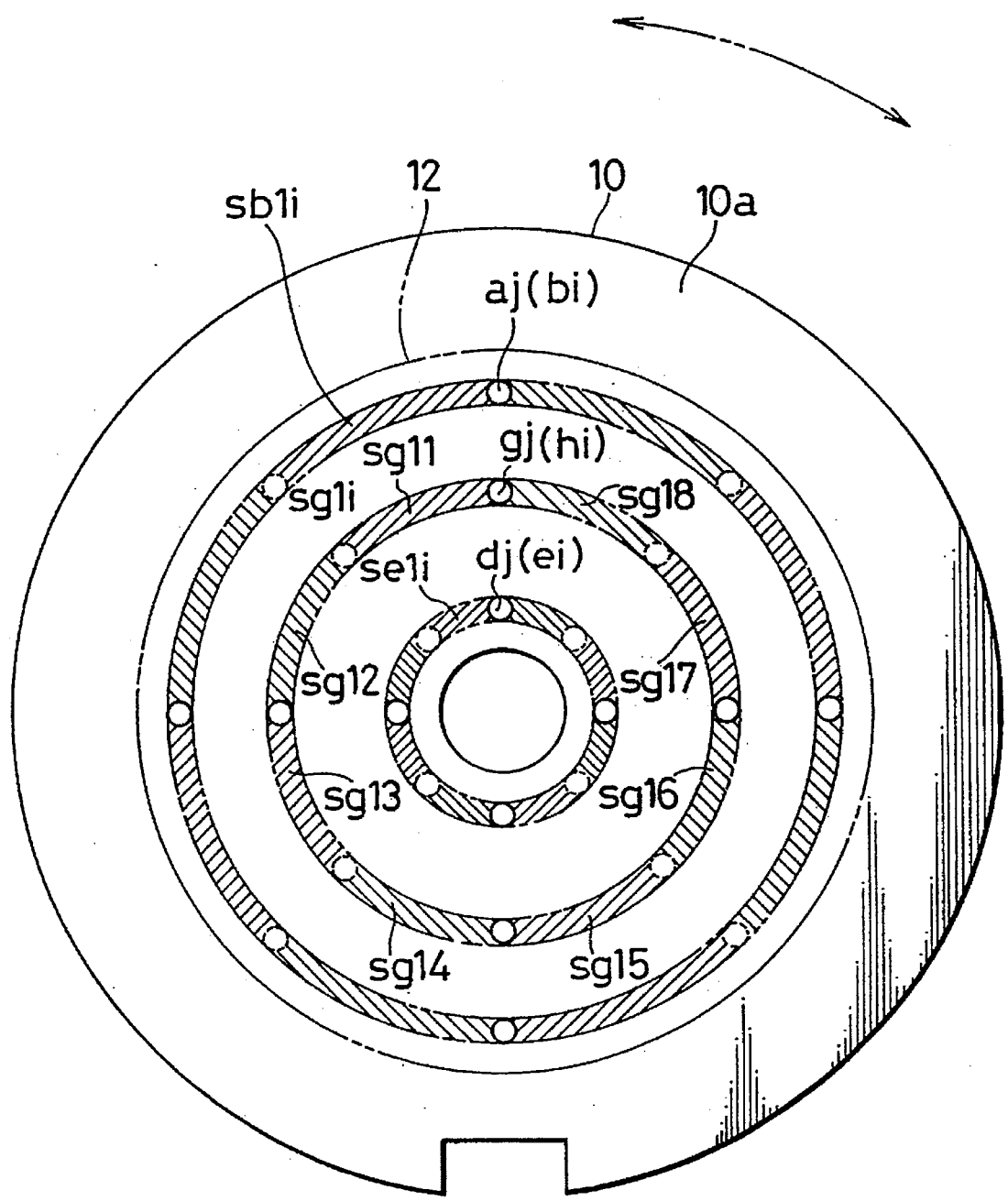
FIG. 4 is a right side view for illustrating different example of one of the fixed elements shown in FIG. 3.

Furthermore, cleaning passageways gj, hi may be provided further on an intermediate area as shown in FIG. 4 to form a cleaning area. In such case, the cleaning effect can be more favorably heightened.

Figure 5:
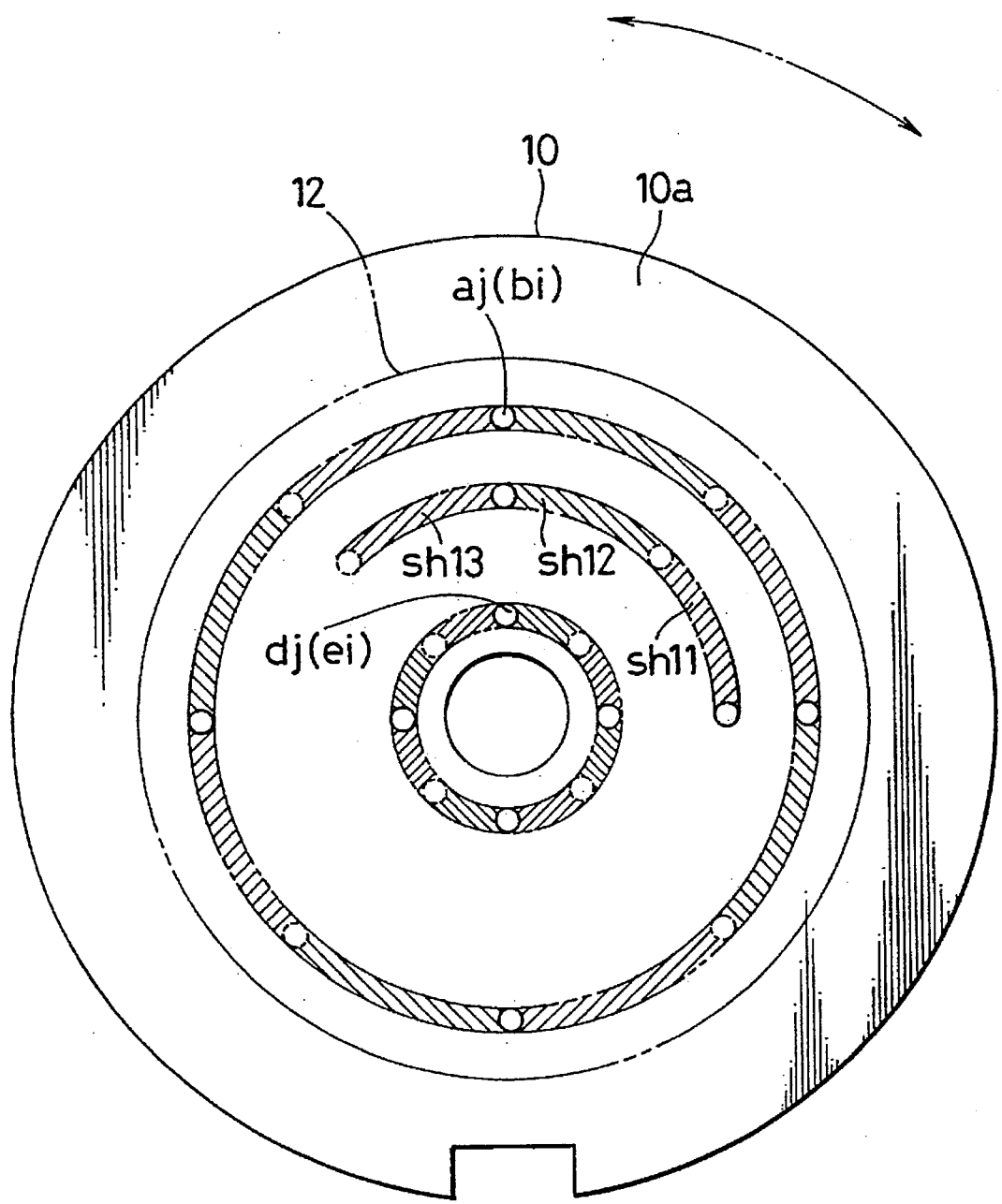
FIG. 5 is a right side view for illustrating different example of one of the fixed elements shown in FIG. 3.
Figure 6:
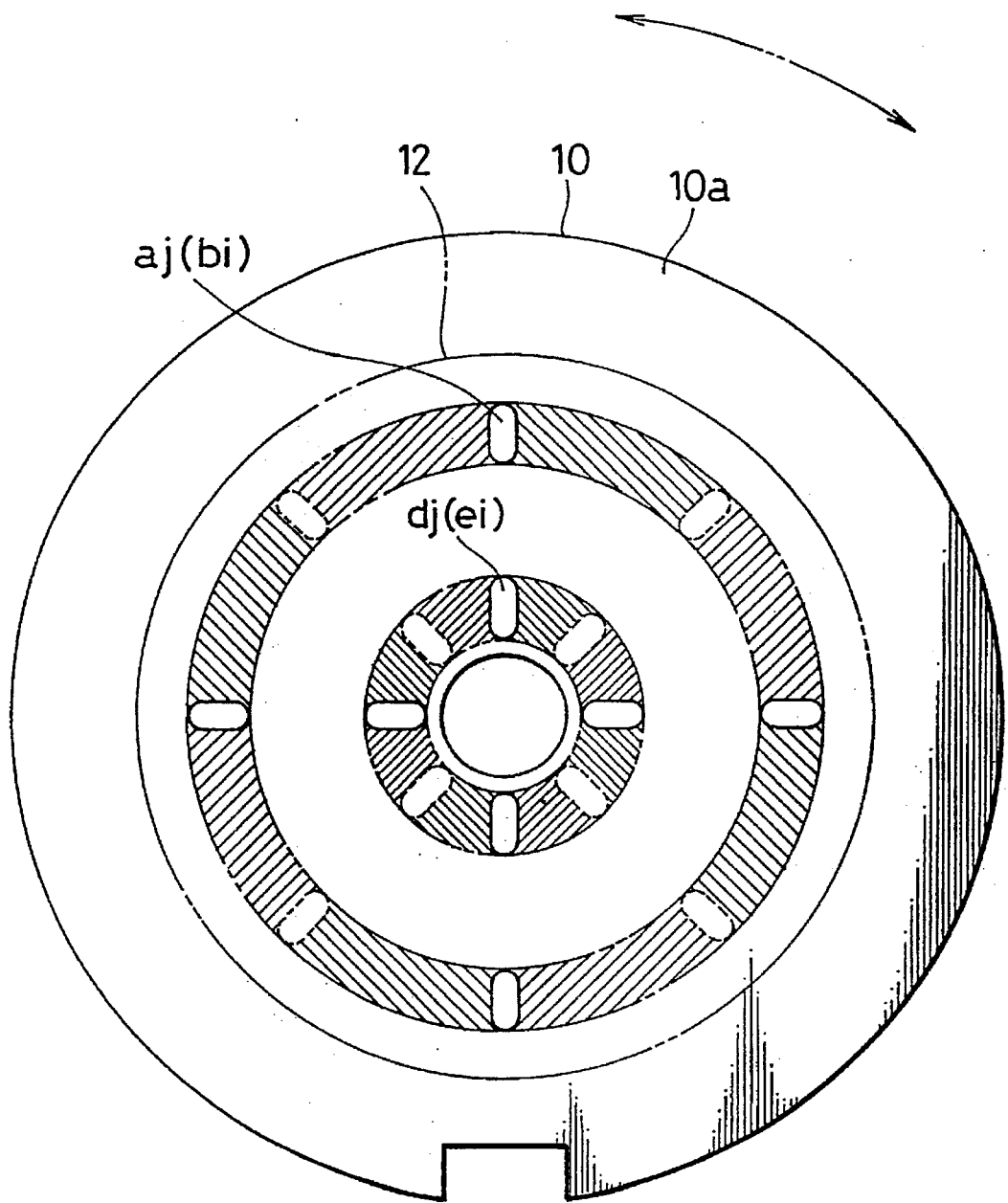
FIG. 6 is a right side view for illustrating still different example of one of the fixed element shown in FIG. 3.

Still furthermore, as shown in FIG. 5, it is possible to intensively clean portions such as Sh11, Sh12 and Sh13 which are liable to be stained.

Even still furthermore, the opening of the cleaning passageways may not be circular, but it may be of other shape. In particular, when the opening is of approximately elliptical configuration radially long, the surface of the elements can be more efficiently cleaned with a small area. Although Embodiment 1 is concerned with a three element construction comprising two fixed elements and one movable element, the same function can be attained with a two element construction comprising one fixed element and one movable element.

Embodiment 2

Figure 7:
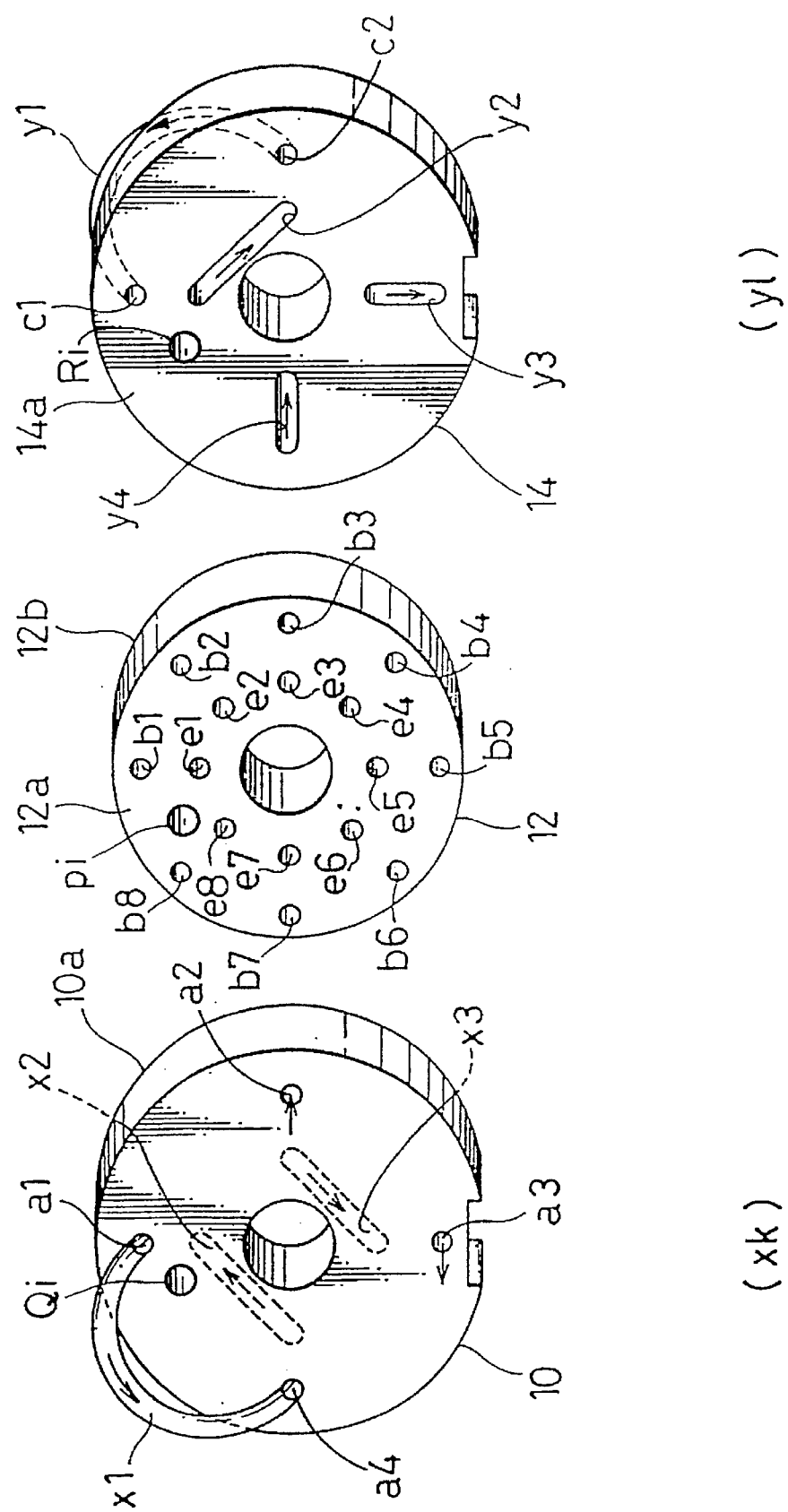
FIG. 7 is a view showing Embodiment 2 of the liquid sampling valve of the present invention, the view being a decomposed perspective view showing the first state thereof.
Figure 8:
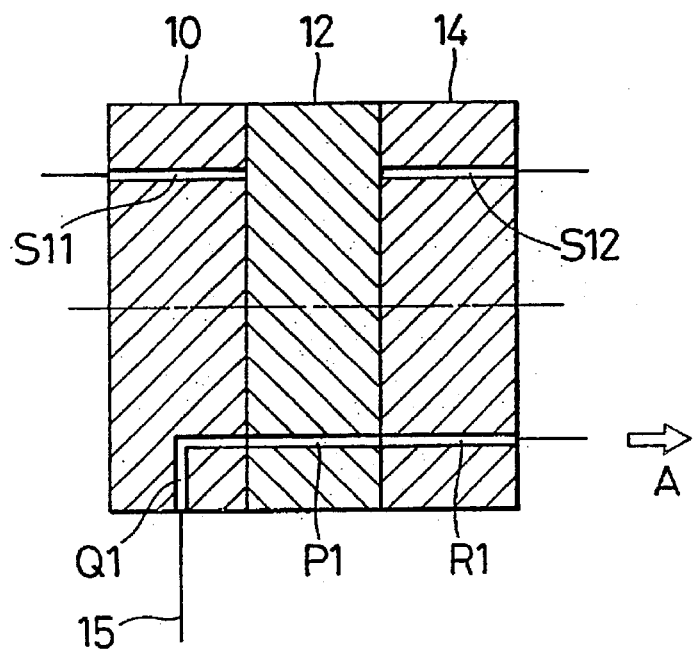
FIG. 8 is a sectional view showing a conventionally used general liquid sampling valve, the view showing the first state thereof.
Figure 9:
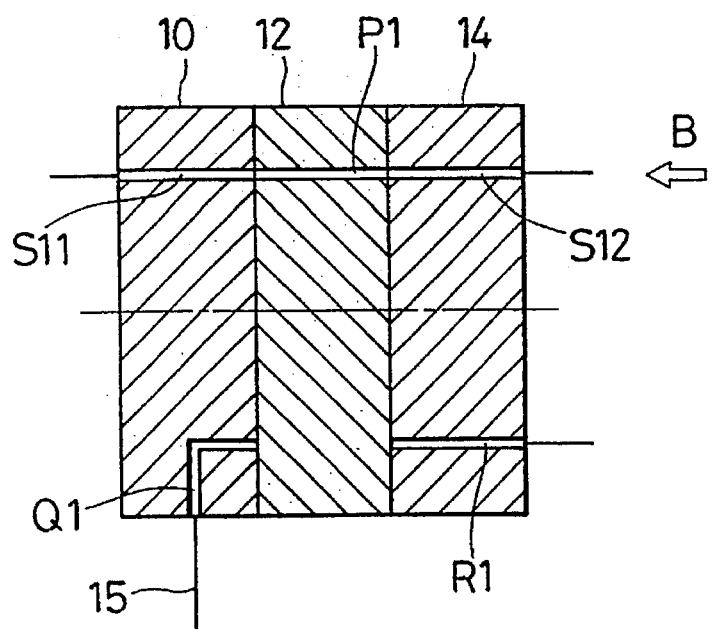
FIG. 9 is a sectional view showing the conventionally used general liquid sampling valve, the view showing the second state thereof.

FIG. 7 is a perspective decomposition view showing other embodiment of the liquid sampling valve of the present invention (showing the first state). However, passageways unrelated to the cleaning of the measuring passageway Pi is omitted.

In Embodiment 1, a cleaning liquid is supplied from passageway aj (a1, a2, a3 and a4), dj (d1, d2, d3 and d4) respectively and is discharged from passageway cj (c1, c2, c3 and c4) and fj (f1, f2, f3 and f4). Thus eight fluid passages have been formed. In Embodiment 2, communication passageways x1, x2, x3, y1, y2, y3 and y4 are newly provided, which connects the eight fluid passages to form one fluid path. Embodiment 2 is intended for simplifying the fluid path system by providing one inlet port and one outlet port.

Referring to FIG. 7, the passageway a2 functions as an inlet port for a cleaning liquid. In the first state, the cleaning liquid flows through passageways b3, c2, y1, c1, b1, a1, x1, a4, b7, y4, e7, x2, e1, y2, e3, x3, e5, y3 and b5 and flows out from the passageway a3 which serves as an outlet port.

As a communication passageway in a liquid sampling valve of the present invention, a loop-like passageway projectingly provided on the outer portion of the element 10, 14 like, for example, passageways as x1 and y1 is preferable. In some cases, the communication passageway may be a groove-like passageway provided on the contact surface of the element 10, 14 like passageways x2, x3, y2, y3 and y4. Apart from them, the loop-like passageway and the groove-like passageway may coexist. Incidentally these communication passageways has no or little cleaning effect even if they actually has. Actually the cleaning effect is not expected of such communication passageways. This can be easily understood from a comparison of groove-like passageways x2, x3, y2, y3 and y4 of the present invention with conventional groove-like passageways in terms of the arrangement and construction thereof. In Embodiment 2, when groove-like passageways x2, x3, y2, y3 and y4 are replaced with loop-like passageways like passageways x1 and y1, the cleaning effect does not show any substantial change. The cleaning effect which is intended in the present invention is produced by a relative movement of openings for cleaning passageways filled with a cleaning liquid on the surface of the element.

The present invention being thus described, it is to be understood that the invention is not limited thereto, but may be otherwise variously embodied and practiced within the scope of the following claims.

What is claimed is:

1. A liquid sampling valve, comprising:
   at least one fixed element having a contact surface; and
   a movable element coaxially arranged with said at least one fixed element, said moveable element having a contact surface for contacting the contact surface of said at least one fixed element,
   one of said elements having at least one measuring passageway extending to the contact surface of the one of said elements, said at least one measuring passageway having at least one opening for receiving and measuring a liquid sample,
   said fixed and movable elements each being provided with a plurality of cleaning passageways for receiving cleaning liquid, wherein each of said cleaning passageways includes an opening on the respective contact surface of the element to which said each passageway corresponds, such that corresponding cleaning passageways communicate upon movement of said movable element, the locations of said cleaning passageways being different distances from central portions of said elements than the location of the at least one opening for said at least one measuring passageway, wherein movement of said movable element relative to said at least one fixed element into a first position allows for the liquid sample to be filled into said at least one measuring passageway, and movement into a second position allows for the liquid sample filled in said at least one measuring passageway to be conveyed out of said fixed and movable elements, wherein said cleaning passageways are arranged such that movement of said movable element relative to said at least one fixed element, when said cleaning passageways contain cleaning liquid, releases cleaning liquid thereby cleaning areas on the contact surfaces of said elements, and wherein said plurality of cleaning passageways in said fixed and movable elements are aligned to form a plurality of fluid paths, and wherein a communicating passageway is further provided to connect these fluid paths.

2. The liquid sampling valve of claim 1, wherein said communicating passageway includes a loop-like passageway.

3. The liquid sampling valve of claim 1, wherein said communicating passageway includes a groove-like passageway.

4. A liquid sampling valve according to claim 2, wherein said loop-like passageway projects out of said at least one fixed element.

5. A liquid sampling valve according to claim 3, wherein said groove-like passageway is located on the contact surface of said at least one fixed element.

* * * * *